United States Patent [19]

Shinma et al.

[11] 4,327,088
[45] Apr. 27, 1982

[54] PHOSPHONOOXY- OR GLYCOSYLOXY-SUBSTITUTED ACRYLOPHENONES, COMPOSITIONS AND USES THEREOF

[75] Inventors: Nobuo Shinma, Clifton, N.J.; Isao Umeda, Yokohama, Japan; Hideo Ishitsuka, Yokohama, Japan; Yasuji Suhara, Yokohama, Japan

[73] Assignee: Hoffmann-La Roche Inc., Nutley, N.J.

[21] Appl. No.: 148,616

[22] Filed: May 12, 1980

[30] Foreign Application Priority Data

May 23, 1979 [GB] United Kingdom ............... 17973/79

[51] Int. Cl.³ .................... A61K 31/66; A61K 31/72; C07F 9/38; C07H 15/20
[52] U.S. Cl. .................................. 424/180; 424/200; 424/202; 424/203; 424/214; 542/412; 542/438; 542/439; 536/4; 260/946; 260/463; 560/108; 560/125
[58] Field of Search ........................ 542/412; 260/946; 424/200, 202, 203, 214, 180; 536/4

[56] References Cited

U.S. PATENT DOCUMENTS 3,686,319  8/1972  Lafon .................................. 424/330
4,122,191 10/1978  Parker ................................ 424/331
4,154,756  5/1979  Shepherd ........................ 260/465 D

FOREIGN PATENT DOCUMENTS 2010180 10/1970  Fed. Rep. of Germany .
1476531  4/1967  France .
 123466 12/1976  German Democratic Rep. .

OTHER PUBLICATIONS

Venturella et al., Chem. Abst. 1961, vol. 55, col. 9412c.
Mahanty et al., Chem. Abst. 1965, vol. 63, col. 4201c.
Haensel et al., Chem. Abst. 1963, vol. 59, col. 9018a.
Stedman's Medical Dictionary, 23rd Ed., Williams & Wilkins, Baltimore, 1976, p. 1560.
Fraser et al., Chem. Abst. 1974, vol. 81, No. 114603h.
Kohler et al., Organic Syntheses, vol. II, Wiley, NY, 1922, pp. 1-3.

*Primary Examiner*—Henry R. Jiles
*Assistant Examiner*—Natalia Harkaway
*Attorney, Agent, or Firm*—Jon S. Saxe; Bernard S. Leon; George W. Johnston

[57] ABSTRACT

Compounds of the formula:

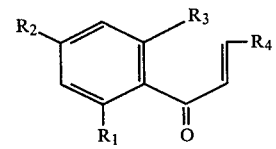

wherein $R_1$ is hydroxy, phosphonooxy, aminoglycosyloxy, acylaminoglycosyloxy, benzyloxycarbonyloxy, arylcarbonyloxy, trialkylammonio-acyloxy or furoyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, alkoxyalkoxy, alkylthio, alkylenedioxy, or acyloxy, with the proviso that when $R_1$ is hydroxy, $R_4$ is benzimidazolyl or phenyl which is substituted by acyloxy or alkoxyalkoxy, or pharmaceutically acceptable salts thereof useful as antiviral agents.

52 Claims, No Drawings

PHOSPHONOOXY- OR GLYCOSYLOXY-SUBSTITUTED ACRYLOPHENONES, COMPOSITIONS AND USES THEREOF

SUMMARY

The invention concerns compounds of the formula:

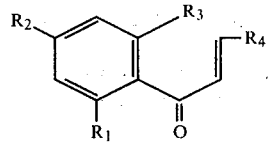

wherein $R_1$ is hydroxy, phosphonooxy, aminoglycosyloxy, acylaminoglycosyloxy, benzyloxycarbonyloxy, arylcarbonyloxy, trialkylammonioacyloxy or furoyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, alkylthio, alkylenedioxy, acyloxy or alkoxyalkoxy, with the proviso that when $R_1$ is hydroxy, $R_4$ is benzimidazolyl or phenyl which is substituted by acyloxy or alkoxyalkoxy, or pharmaceutically acceptable salts thereof.

The compounds of formula I are useful in treating mammals having infections caused by viruses such as human rhinoviruses, enteroviruses and influenzaviruses. The inventive compounds can be administered in antiviral pharmaceutical compositions.

DETAILED DESCRIPTION OF THE INVENTION

The invention concerns substituted acetophenones and pharmaceutical compositions containing same, which are useful as antiviral agents.

As used herein, alkyl connotes straight or branched chain saturated aliphatic hydrocarbon groups of 1 to 20 carbon atoms. Lower alkyl denotes alkyl groups of 1 to 6 carbon atoms such as methyl, ethyl, n-propyl, isopropyl and hexyl.

Alkoxy denotes straight or branched chain alkoxy groups of 1 to 20 carbon atoms. Lower alkoxy connotes alkoxy groups having 1 to 4 carbon atoms such as methoxy, ethoxy, isopropoxy, propoxy and butoxy.

Halogen denotes fluorine, chlorine, bromine or iodine. Halides connote fluoride, chloride, bromide or iodide.

Alkylenedioxy denotes a moiety derived by the condensation of the hydroxy group of a 1,2 or 1,3 diol with a carbonyl function. The alkylene group of alkylenedioxy is a straight or branched chain alkylene group having 2 to 20 carbon atoms. Lower alkylenedioxy is a alkylenedioxy radical wherein its alkylene group has 2 to 5 carbon atoms. Typical lower alkylenedioxy groups are methylenedioxy, ethylenedioxy, 1,2-propylenedioxy, 2,4-butylenedioxy and 2,3-pentylenedioxy.

Aryl denotes mononuclear and polynuclear aromatic hydrocarbon groups which can be unsubstituted or substituted in one or more positions with halogen, nitro, alkylthio, acyloxy, alkoxyalkoxy, lower alkylenedioxy, lower alkyl or lower alkoxy. Suitable mononuclear aromatic hydrocarbon groups are phenyl and the like.

Typical polynuclear aromatic hydrocarbon groups are napthyl, anthryl, phenanthryl, azulyl and the like.

Carboxylic acids are alkanoic carboxylic acids and aromatic carboxylic acid of the formula:

wherein R is hydrogen, alkyl or aryl.
Preferably R is hydrogen, lower alkyl or phenyl. Examples of carboxylic acids are formic acid, acetic acid, isopropionic acid, benzoic acid and the like.

Acyl connotes a radical derived from a carboxylic acid and has the formula:

wherein R is hydrogen, alkyl or aryl.
Preferably, R is hydrogen, lower alkyl or phenyl. Typical acyl groups are formyl, acetyl, propionyl, butyryl, benzoyl and the like.

Acyloxy denotes a radical derived from a carboxylic acid and has the formula:

wherein R is hydrogen, alkyl or aryl.
Preferably, R is hydrogen, lower alkyl or phenyl. Typical acyloxy groups are formyloxy, acetoxy, propionyloxy, butyryloxy, benzoyloxy and the like.

Trialkylammonioacyloxy denotes a radical of the formula:

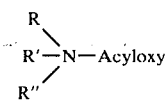

wherein R,R' and R" each are alkyl, and acyloxy is as defined above. Triethylammonioacetoxy is a particularly preferred trialkylammonioacyloxy.

Glycosyloxy connote radicals derived from monosaccharides of 5 to 7 carbon atoms by removal of the hydrogen from the anomeric hydroxy group of the monosaccharides. Preferred glycosyloxy groups are glucosyloxy, mannosyloxy and galactosyloxy.

Aminoglycosyloxy denotes a radical comprising an amino group ($-NH_2$) and a glycosyloxy group as defined above. Preferred aminoglycosyloxy moieties are glucosaminyloxy, mannosaminyloxy and galactosaminyloxy.

Acylaminoglycosyloxy denotes a group comprising acyl and aminoglycosyloxy moieties as defined above, wherein the aminoglycosyloxy group is acylated. Preferred acyl aminoglycosyloxy radicals are peracetyl-$\beta$-D-glucosaminyloxy, N-acetyl-$\beta$-D-glucosaminyloxy and the like.

Arylcarbonyloxy denotes a radical comprising a carbonyloxy moiety

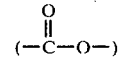

and an aryl group, as defined above. The "aryl" moiety of the arylcarbonyloxy group can be unsubstituted or substituted with the moieties described above. Preferred arylcarbonyloxy radicals are benzoyloxy, 4-methoxybenzoyloxy, 2,4-dimethoxybenzoyloxy and the like.

Alkali metals include lithium, sodium, potassium and rubidium. Alkali metal hydroxides include lithium hydroxide, sodium hydroxide and the like. Alkaline earth metals include barium, magnesium, calcium and strontium.

The substituted acetophenones of the invention have the formula:

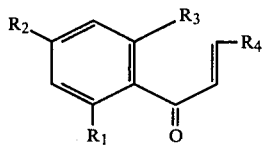

wherein $R_1$ is hydroxy, phosphonooxy, aminoglycosyloxy, acylaminoglycosyloxy, benzyloxycarbonyloxy, arylcarbonyloxy, trialkylammonioacyloxy or furoyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, alkylthio, alkylenedioxy, acyloxy or alkoxyalkoxy, with the proviso that when $R_1$ is hydroxy, $R_4$ is benzimidazolyl or phenyl which is substituted with acyloxy or alkoxyalkoxy, or pharmaceutically acceptable salts thereof.

In compound I, the $R_4$ moieties can be attached to the remaining structure of compound I at any carbon atom on the $R_4$ ring. Further, the various substituents which can be positioned on the $R_4$ rings can be attached to any carbon atom on the ring. The resulting compounds are contemplated by the invention and possess antiviral activity.

More particularly, the benzimidazolyl moiety can be attached to the remaining structure of compound I at any carbon atom of benzimidazolyl. It is preferred to attach benzimidazolyl at its fifth carbon atom (i.e., 5-benzimidazolyl).

The furyl or thienyl moiety can be attached to the remaining structure of compound I at any carbon atom of the furyl or thienyl ring. It is preferred to attach the moieties at the second carbon atom of the ring (i.e, 2-furyl; 2-thienyl). When $R_4$ is substituted furyl or substituted thienyl, the lower alkyl substituent may be attached to any carbon atom of the furyl or thienyl ring. Preferably, the substituent is attached at the fifth carbon atom of the ring (e.g., 5-methyl-2-furyl).

When $R_4$ is substituted phenyl, the substituents may be attached to any carbon atom of the phenyl ring. More than one of the same substituents may be attached to the phenyl ring. Preferred substituted phenyl radicals are p-tolyl, p-methoxyphenyl, p-ethoxyphenyl, p-methoxymethoxyphenyl, p-acetoxyphenyl, m,p-(methylenedioxy)phenyl, p-(methylthio)phenyl.

In one aspect of the invention, the substituents $R_1$–$R_4$ of formula I can be represented as follows:

$R_1$ is phosphonooxy, benzyloxycarbonyloxy, benzoyloxy, triethyl ammonioacetoxy or furoyloxy; $R_2$ and $R_3$ each are lower alkoxy; and $R_4$ is 5-benzimidazolyl, 2-furyl, 5-methyl-2-furyl, 2-thienyl or p-tolyl, p-methoxyphenyl or o-p-dimethoxyphenyl.

Pharmaceutically acceptable salts of formula I such as alkali metal and alkaline earth metal salts are included within the invention.

Representative compounds of formula I are:
2′,4,4′-trimethoxy-6′-(phosphonooxy)chalcone;
4-ethoxy-2′,4′-dimethoxy-6′-(phosphonooxy)chalcone;
2′,4′-dimethoxy-4-methyl-6′-(phosphonooxy)chalcone;
2′,4′-dimethoxy-4-(methylthio)-6′-(phosphonooxy)chalcone;
2′-ethoxy-4,4′-dimethoxy-6′-(phosphonooxy)chalcone;
2′,4′-dimethoxy-3-(5-methyl-2-furyl)-6′-(phosphonooxy)acrylophenone;
4′-ethoxy-2′,4-dimethoxy-6′-(phosphonooxy)chalcone;
2′,4′-dimethoxy-3,4-(methylenedioxy)-6′-(phosphonooxy)chalcone;
2′,4′-dimethoxy-6′-(phosphonooxy)-3-(2-thienyl)acrylophenone;
2′-(2-acetamido-2-deoxy-3,4,6-tri-O-acetyl-β-D-glucopyranosyloxy)-4,4′,6′-trimethoxychalcone;
2′-(2-acetamido-2-deoxy-β-D-glucopyranosyloxy)-4,4′,6′-trimethoxychalcone;
2′-(benzyloxycarbonyloxy)-4,4′,6′-trimethoxychalcone;
2′,4,4′-trimethoxy-6′-(triethylammonioacetoxy)chalcone;
2′,4,4′-trimethoxy-6′-(4-methoxybenzoyloxy)chalcone;
2′-(2,4-dimethoxybenzoyloxy)-4,4′,6′-trimethoxychalcone;
2′-(benzoyloxy)-4,4′,6′-trimethoxychalcone;
2′-(furoyloxy)-4,4′,6′-trimethoxychalcone;
2′-hydroxy-4′,6′-dimethoxy-4-(methoxymethoxy)chalcone;
3-(5-benzimidazolyl)-2′-hydroxy-4′,6′-dimethoxyacrylophenone;
4-acetoxy-2′-hydroxy-4′,6′-dimethoxychalcone.

The compounds of formula I are useful in treating mammals having infections caused by viruses such as human rhinoviruses, enteroviruses, influenzaviruses and the like. Certain viruses of the Picorna group are particularly affected by the inventive compounds. Compound I is also effective in treating the common cold as well as its symptoms. Furthermore, the compounds of formula I can be used as medicaments against viral disease, in the form of pharmaceutical preparations.

The pharmaceutical compositions of the invention contain at least one of the antiviral compounds of formula I with a compatible pharmaceutical carrier material. Any conventional carrier can be utilized. The carrier can be an organic or inorganic inert carrier material suitable for enteral, percutaneous or parenteral administration. Suitable carriers include water, gelatin, gum arabic, lactose, starch, magnesium stearate, talc, vegetable oils, polyalkyleneglycols, petroleum jelly and the like. Furthermore, the pharmaceutical preparations may contain other pharmaceutically active agents such as febrifuge, anodyne, anti-inflammatory, anti-histamine, interferon inducer and the like.

The pharmaceutical preparations can be made up in any conventional form including: (a) a solid form for oral administration such as tablets, capsules, pills, powders, granules and the like; (b) a liquid for nasal or oral administration such as solutions, syrups, suspensions, elixirs and the like; (c) preparations for parenteral administration such as sterile solutions, suspensions or emulsions; and (d) preparations for topical administrations such as solutions, suspensions, ointments, micronized powders, aerosols, emulsions, gargles, troches and the like. The pharmaceutical preparations may be sterilized and/or may contain adjuvants such as preservatives, stabilizers, wetting agents, emulsifiers, salts for varying the osmotic pressure or buffers.

In general, compound I amounts to about 0.001% to about 70.0% by weight of the inventive compositions.

The dosage for treatment with the inventive antiviral compositions depends on the route of administration, age, weight, and condition of the patient, and the particular disease to be treated. A typical adult dosage (e.g., for use in common cold) is about 100 to 2,000 mg of the composition, 3 to 6 times daily for oral or parenteral treatment and about 0.1 to 100 μg of the compound/cm² of surface area, 3 to 6 times daily for a topical application.

If desired, the pharmaceutical preparations can be administered so that the concentration of compound I is greater than the minimum inhibitory concentration for the particular viral infection being treated.

In accordance with a further aspect of the invention, compound I (or the above described pharmaceutical compositions containing same) can be administered to mammals such as humans to treat the mammals infected with viruses such as human rhinoviruses, enteroviruses, influenzaviruses and the like.

The following compounds of formula I are particularly suitable for nasal administration or injection because they are soluble in water:

2',4,4'-trimethoxy-6'-(phosphonooxy)chalcone;
4-ethoxy-2',4'-dimethoxy-6'-(phosphonooxy)chalcone;
2',4'-dimethoxy-4-methyl-6'-(phosphonooxy)chalcone;
2',4'-dimethoxy-4-(methylthio)-6'-(phosphonooxy)chalcone;
2'-ethoxy-4,4'-dimethoxy-6'-(phosphonooxy)chalcone;
2',4'-dimethoxy-3-(5-methyl-2-furyl)-6'-(phosphonooxy)acrylophenone;
4'-ethoxy-2',4-dimethoxy-6'-(phosphonooxy)chalcone;
2',4'-dimethoxy-3,4-(methylenedioxy)-6'-(phosphonooxy)chalcone;
2',4'-dimethoxy-6'-(phosphonooxy)-3-(2-thienyl)acrylophenone;
2'-(2-acetamido-2-deoxy-β-D-glucopyranosyloxy)-4,4',6'-trimethoxychalcone;
2',4,4'-trimethoxy-6'-(triethylammonioacetoxy)chalcone.

In drops for intranasal application, an acceptable range of concentration of the active ingredient of compound I is about 0.01 to about 1 mg/ml.

Compound I is administered in the aforementioned doses. In particular, the compounds of formula I can be given at a daily dose of about 1 mg. to about 100 mg. of compound per kilogram of body weight of the mammal.

As previously discussed, compound I possesses antiviral activity. To examine this activity, in vivo and in vitro experiments were performed on compound I and the test results are summarized in Examples 21-25 below. It is found that the substituted acetophenones of formula I exhibit significant antiviral utility. In particular, the compounds inhibit the replication of human rhinoviruses in human embryonic lung cell or HeLa cell culture at 0.006~1 μg of compound/ml of pharmaceutical composition.

In addition to the above, the compounds of formula I are well tolerated for a maintenance of tissue culture cells and do not show any toxic activity at 10 to 1,000 times higher concentrations than that of their effective dose against infection such as rhinovirus infection. When administered by oral route in ddy mice, the compounds did not show any toxic symptoms at dose of 1 g/kg of body weight or more. See Example 25 below.

In a further aspect of the invention, compound I can be produced by:

(a) reacting a compound of the formula:

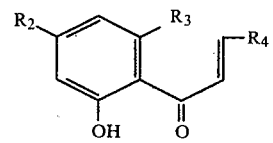

wherein R₂, R₃ and R₄ are as defined above, with a phosphorus oxyhalide in a solvent in the presence of a base, and hydrolyzing the resulting compound;

(b) reacting compound II with a 2-acetamido-2-deoxy-3,4,6-tri-O-acetyl-α-D-glucopyranosyl halide in a solvent in the presence of an alkali hydride, and if necessary, partially hydrolyzing the resulting compound;

(c) reacting compound II with a trialkylamine and a haloacetyl halide, in a solvent;

(d) acylating the hydroxyl radical in compound II with a reactive derivative of a benzyloxycarboxylic acid, a substituted or unsubstituted arylcarboxylic acid or a furancarboxylic acid;

(e) acylating a hydroxyl radical at the 4-position in a compound of the formula:

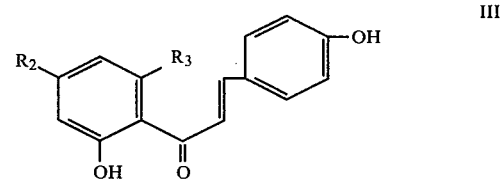

wherein R₂ and R₃ are as defined above, with a reactive derivative of an alkanoic acid; or (f) reacting a compound of the formula:

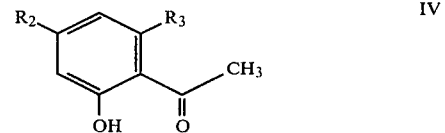

wherein R₂ and R₃ are as defined above,
with an aldehyde of the formula:

     V wherein R₄ is as defined above,
in a solvent in the presence of a basic catalyst.

The above process (a)-(f) can be carried out by any conventional technique using standard reactants.

Illustratively, the process in accordance with embodiment (a) can be carried out by reacting compound II with a phosphorus oxyhalide such as phosphorus oxychloride or oxybromide in a solvent such as benzene, toluene, tetrahydrofuran, dioxane, cyclohexane and the like, in the presence of a base such as N,N-diisopropylethylamine, triethylamine, pyridine and the like. The resulting compound is hydrolyzed by standard procedures.

The reaction in accordance with embodiment (b) can be effected by adding a 2-acetoamido-2-deoxy-3,4,6-tri-O-acetyl-α-D-glucopyranozyl halide to a solution of compound II and an alkali hydride such as sodium hydride, potassium hydride and the like in a solvent such as dimethylformamide, dioxane, tetrahydrofuran, benzene and the like. If desired, the resulting product can be hydrolyzed by conventional procedures to remove the acetyl radicals other than that of the acetamido radical.

The reaction in accordance with embodiment (c) can be carried out by adding a trialkylamine and a haloacetyl halide (e.g., triethylamine and bromoacetyl bromide) to a solution of compound II and an organic solvent (e.g., ethyl acetate).

The acylation of the hydroxyl radical in compound II in accordance with embodiment (d) can be carried out in any conventional manner. A typical procedure includes treating compound II with a reactive derivative of a benzyloxycarboxylic acid, a substituted or unsubstituted arylcarboxylic acid or a furancarboxylic acid. Preferred reactive derivatives are bis(4-methoxybenzoic)anhydride, benzoyl chloride, benzyloxycarbonyl chloride, 2,4-dimethoxybenzoyl chloride, 2-furoyl chloride and the like.

The acylation of the hydroxyl radical at the 4-position in compound II in accordance with embodiment (e) can be effected in any conventional manner. A suitable technique includes treating compound III with a reactive derivative of an alkanoic acid (for example, acetic anhydride).

The reaction in accordance with embodiment (f) can be carried out by adding a basic catalyst, (e.g., an alkali, such as sodium hydroxide, potassium hydroxide, sodium carbonate or potassium carbonate) or an alcoholate (e.g., sodium ethoxide and potassium ethoxide) to a solution of compounds IV and V in an organic solvent (e.g., methanol, ethanol, dioxane, tetrahydrofuran, benzene or hexane) and stirring the mixture for several hours to 3 days at aobut 0°~100° C.

Compounds II–V are known or can be prepared from known compounds by conventional procedures. For example, compound II can be prepared by the process of embodiment (f).

The following Examples further illustrate the invention. All temperatures are in degrees Centigrade. Room temperature is about 23° C. Ether connotes diethyl ether. In the Examples, the term LD$_{50}$ means the amount (mg./kg. of body weight) of ingredient which would kill 50% of the test animals.

EXAMPLE 1

To a stirred solution containing 1.0 g (3.18 m moles) of 2'-hydroxy-4,4',6'-trimethoxychalcone and 2 ml of N,N-diisopropylethylamine in 20 ml of anhydrous toluene, there were added 10 ml of phosphorus oxychloride. After being stirred at room temperature for 50 minutes, the mixture was evaporated under reduced pressure at a bath temperature of 30°~40° C. to give a brown oily substance.

The substance was dried over phosphorus pentoxide overnight. The dried residue was hydrolyzed in 50 ml of a mixed solvent of water and tetrahydrofuran (1:1, v/v) for 10 minutes at room temperature. The organic solvent was removed under reduced pressure at a bath temperature of 30°~40° C. The aqueous concentrate was extracted with three 50 ml portions of ice-cooled chloroform. The combined extracts were dried over sodium sulfate and the solvent was removed under reduced pressure to give a brownish residue.

The residue was dissolved in 30 ml of 0.1 N potassium carbonate, and the solution was washed with two 50 ml portions of ethyl acetate, acidified with cold hydrochloric acid and then extracted with three 50 ml portions of chloroform. The combined extracts were dried over sodium sulfate and concentrated under reduced pressure to a volume of about 10 ml. The concentrate was applied onto a column of silica gel (40 g), and the column was eluted with chloroform-methanol (10:1, v/v). The fractions 30–50 (each fraction: 10 ml). were combined and evaporated under reduced pressure to give 0.65 g of yellow residue. Crystallization of the residue from ethanol-hexane yielded 0.55 g (44% yield) of 2',4,4'-trimethoxy-6'-(phosphonooxy)chalcone as reddish brown crystals: mp 71°~73° C.

EXAMPLE 2

In a manner analogous to that described in Example 1 except that 4-ethoxy-2'-hydroxy-4',6'-dimethoxychalcone was used in place of 2'-hydroxy-4,4',6'-trimethoxychalcone, there was obtained 4-ethoxy-2',4'-dimethoxy-6'-(phosphonooxy)chalcone: mp 63°~64° C.

EXAMPLE 3

In a manner analogous to that described in Example 1 except that 2'-hydroxy-4',6'-dimethoxy-4-methylchalcone was used, there was obtained 2',4'-dimethoxy-4-methyl-6'-(phosphonooxy)chalcone: mp 81°~83° C.

EXAMPLE 4

In a manner analogous to that described in Example 1 except that 2'-hydroxy-4',6'-dimethoxy-4-(methylthio)-chalcone was used, there was obtained 2',4'-dimethoxy-4-(methylthio)-6'-(phosphonooxy)chalcone: mp 63°~66° C.

EXAMPLE 5

In a manner analogous to that described in Example 1 except that 2'-ethoxy-6'-hydroxy-4,4'-dimethoxychalcone was used, there was obtained 2'-ethoxy-4,4'-dimethoxy-6'-(phosphonooxy)chalcone: mp 72°~75° C.

EXAMPLE 6

In a manner analogous to that described in Example 1 except that 2'-hydroxy-4',6'-dimethoxy-3-(5-methyl-2-furyl)acrylophenone was used, there was obtained 2',4'-dimethoxy-3-(5-methyl-2-furyl)-6'-(phosphonooxy)acrylophenone: $^1$H-nmr(CDCl$_3$) δ3.8(3H, OCH$_3$), 3.85(3H, OCH$_3$) and 2.9 ppm (3H, CH$_3$ in furan moiety).

EXAMPLE 7

In a manner analogous to that described in Example 1 except that 4'-ethoxy-2'-hydroxy-4,6-dimethoxychalcone was used, there was obtained 4'-ethoxy-2',4-dimethoxy-6'-(phosphonooxy)chalcone: mp 85°~88° C.

EXAMPLE 8

In a manner analogous to that described in Example 1 except that 2'-hydroxy-4',6'-dimethoxy-3,4-(methylenedioxy)chalcone was used, there was obtained 2',4'-dimethoxy-3,4-(methylenedioxy)-6'-(phosphonooxy)chalcone: mp 79°~80° C.

EXAMPLE 9

In a manner analogous to that described in Example 1 except that 2'-hydroxy-4',6'-dimethoxy-3-(2-thienyl)acrylophenone was used, there was obtained 2',4'-dimethoxy-6'-(phosphonooxy)-3-(2-thienyl)acrylophenone.

EXAMPLE 10

To a stirred mixture containing 500 mg of 2'-hydroxy-4',6'-trimethoxychalcone and 100 mg of sodium hydride (50% purity) in 10 ml of anhydrous dimethylformamide, there were added 1.1 g of 2-acetoamido-2-deoxy-3,4,6-tri-O-acetyl-α-D-glucopyranosyl chloride. The stirring was continued for 3 hours.

After that, 30 ml of ice-water and 50 ml of chloroform were added thereto, and the mixture was shaken. The chloroform phase was separated, washed with three 20 ml portions of ice-water, dried over sodium sulfate and then evaporated under reduced pressure. The residue was dissolved in a small amount of ethyl acetate, and the solution was applied onto a column of silica gel (30 g). The column was eluted with ethyl acetate. Fractions 20~25 (each fraction: 10 ml) were combined and evaporated to give 406 mg of solid. Crystallization of said substance from ethyl acetate-hexane yielded 301 mg (30% yield) of 2'-(2-acetamido-2-deoxy-3,4,6-tri-O-acetyl-β-D-glucopyranosyloxy)-4,4',6'-trimethoxychalcone as pale yellow crystals: mp 108°~110° C.

EXAMPLE 11

300 mg of 2'-(2-acetamido-2-deoxy-3,4,6-tri-O-acetyl-β-D-glucopyranosyloxy)-4,4',6'-trimethoxychalcone obtained in Example 10 were dissolved in 4 ml of methanol. To the solution, there were added 0.3 ml of triethylamine and 0.4 ml of water. After being stirred at room temperature for 18 hours, the mixture was evaporated under reduced pressure.

Crystallization of the residue from ethanol-hexane yielded 180 mg of 2'-(2-acetamido-2-deoxy-β-D-glucopyranosyloxy)-4,4',6'-trimethyloxychalcone as pale yellow crystals: mp 197°~200° C.

EXAMPLE 12

To a solution of 100 mg of 2'-hydroxy-4,4',6'-trimethoxychalcone in 2 ml of ethyl acetate, there were added 0.2 ml of triethylamine and 0.12 ml of bromoacetyl bromide. After being stirred at room temperature for 30 minutes, the mixture was diluted with 5 ml of dimethylformamide, and the stirring was continued for further 3 hours.

After that, 50 ml of ether were added thereto, and the resulting precipitate was collected by decantation and dissolved in 5 ml of water. Passing the solution through a column of anionic exchange resin (Dowex 1 (Cl form, 1×20 cm)), followed by lyophilization of the passed solution gave 50 mg of pale yellow hygroscopic powder.

Crystallization of said powder from methanol-ethyl acetate yielded 32 mg of 2',4,4'-trimethoxy-6'-(triethylammonioacetoxy) chalcone chloride as yellow crystals.

EXAMPLE 13

To a solution of 2'-hydroxy-4,4',6'-trimethoxychalcone in 5 ml of anhydrous tetrahydrofuran, there were added 10 ml of triethylamine, 43 mg of p-(dimethylamino)pyridine and 182 mg of bis(4-methoxybenzoic anhydride.

After being stirred at 80° C. for 18 hours, the mixture was evaporated. 30 ml of ethyl acetate were added to the residue, and the mixture was washed successively with 0.2 N hydrochloric acid, 10% by volume sodium carbonate and water. The ethyl acetate phase was separated, dried over sodium sulfate and evaporated. The residue was then subjected to chromatography on silica gel (6 g) which was eluted with hexane-ethyl acetate (3:1 to 1:1 v/v). Thus, 180 mg of pale yellow oil were obtained.

Crystallization of the oil from methanol yielded 110 mg of 2',4,4'-trimethoxy-6'-(4-methoxybenzoyloxy)-chalcone as pale yellow prisms: mp 111°~111.5° C.

EXAMPLE 14

To a solution containing 156 mg (1.1 m moles) of benzoyl chloride, 220 mg (2.2 m moles) of triethylamine and 20 mg (0.16 m mole) of 4-(dimethylamino)pyridine in 5 ml of anhydrous tetrahydrofuran, there were added 314 mg (1 m mole) of 2'-hydroxy-4,4',6'-trimethoxychalcone. The mixture was vigorously stirred at room temperature for 10 minutes and then poured into 50 ml of ice-cooled 0.1 N hydrochloric acid.

The mixture was extracted with two 70 ml portions of ethyl acetate, and the combined extracts were dried over sodium sulfate. Removal of the solvent followed by recrystallization of the residue from methanol gave 315 mg (75% yield) of 2'-(benzoyloxy)-4,4',6'-trimethoxychalcone as pale yellow needles: mp 133.8° C.

EXAMPLE 15

In a manner analogous to that described in Example 14 except that benzyloxycarbonyl chloride was used in place of benzoyl chloride, there was obtained 2'-(benzyloxycarbonyloxy)-4,4',6'-trimethoxychalcone as pale yellow crystals: mp 127.2° C.

EXAMPLE 16

In a manner analogous to that described in Example 14 except that 2,4-dimethoxybenzoyl chloride was used, there was obtained 2'-(2,4-dimethoxybenzoyloxy)-4,4',6'-trimethoxychalcone as colorless prisms: mp 119°~120° C.

EXAMPLE 17

In a manner analogous to that described in Example 14 except that 2-furoyl chloride was used, there was obtained 2'-(furoyloxy)-4,4',6'-trimethoxychalcone as pale yellow crystals: mp 127.0° C.

EXAMPLE 18

To a stirred solution containing 1.57 g (8 m moles) of 2'-hydroxy-4',6'-dimethoxyacetophenone and 1.33 g (8 m moles) of 4-(methoxymethoxy)benzaldehyde in 3 ml of ethanol, there were added 30 ml of 15% by volume aqueous sodium hydroxide. After being stirred at room temperature for 2 days, the mixture was poured into 70 ml of ice-water. The pH was adjusted to 7 by adding hydrochloric acid, and the mixture was extracted with two 150 ml portions of dichloromethane. The combined extracts were washed with water, dried over sodium sulfate and then evaporated. The oily residue was crystallized from methanol to yield 780 mg of 2'-hydroxy-4',6'-dimethoxy-4-(methoxymethoxy)chalcone as yellow needles: mp 104.5° C.

EXAMPLE 19

In a manner analogous to that described in Example 18 except that 5-benzimidazolecarbaldehyde was used in place of 4-(methoxymethoxy)benzaldehyde, there was obtained 3-(5-benzimidazolyl)-2'-hydroxy-4',6'-dimethoxyacrylophenone as crystals: mp 147°~149° C.

EXAMPLE 20

A mixture of 207 mg of 2',4-dihydroxy-4',6'-dimethoxychalcone, 60 mg of sodium acetate and 70 mg of acetic anhydride was heated at 90° C. for one hour. The mixture was evaporated under reduced pressure, and the residue was extracted with 30 ml of chloroform. Removal of the solvent from the extract and recrystallization of the residue from methanol yielded 157 mg of 4-acetoxy-2'-hydroxy-4',6'-dimethoxychalcone: mp 141.8° C.

Test results of antiviral activity studies on compounds of the invention are described in following Examples 21–22 (in vitro antiviral activity) and Examples 23–25 (in vivo antiviral activity).

EXAMPLE 21

Inhibition of viral cytopathogenic effect

A suspension of HeLa cells ($6 \times 10^4$) was mixed with rhinovirus HGP ($3 \times 10^3$ PFU) (plaque forming units) and was plated in a microtest plate where serially diluted compounds to be tested were contained. The cells were then cultured with Eagle's minimum essential medium containing 2% calf serum, 1% tryptose phosphate broth, 100 μg/ml of streptomycin sulfate and 20 unit/ml of penicillin G. Viral c.p.e. (cytopathogenic effect) was observed by a microscope after 2 days culture at 33° C

EXAMPLE 22

The results of Example 21 are shown in Table 1. The antiviral activity of the tested compounds is expressed by the minimal inhibitory concentration at which dose viral c.p.e. is inhibited by 50% as compared to the control culture. As shown in Table I, the compounds provided by the present invention exhibit the activity against rhinovirus infection in cell culture.

TABLE 1

| Compounds | Minimal Inhibitory Concentration ($\mu g/m^2$) against rhinovirus HGP |
|---|---|
| 2',4,4'-trimethoxy-6'-(phosphonooxy)chalcone | 0.03 ~ 0.1 |
| 4-ethoxy-2',4'-dimethoxy-6'-(phosphonooxy)chalcone | 0.006 ~ 0.02 |
| 2',4'-dimethoxy-4-methyl-6'-(phosphonooxy)chalcone | 0.02 |
| 2',4'-dimethoxy-4-(methylthio)-6'-(phosphonooxy)chalcone | 0.02 |
| 2'-ethoxy-4,4'-dimethoxy-6'-(phosphonooxy)chalcone | 0.02 |
| 2',4'-dimethoxy-3-(5-methyl-2-furyl)-6'-(phosphonooxy)acrylophenone | 0.04 ~ 0.1 |
| 4'-ethoxy-2',4-dimethoxy-6'-(phosphonooxy)chalcone | 0.03 |
| 2',4'-dimethoxy-3,4-(methylenedioxy)-6'-(phosphonooxy)chalcone | 0.06 |
| 2',4'-dimethoxy-6'-(phosphonooxy)-3-(2-thienyl)acrylophenone | 0.04 ~ 0.1 |
| 2'-(2-acetamido-2-deoxy-3,4,6-tri-O-acetyl-β-D-glucopyranosyloxy)-4,4',6'-trimethoxychalcone | 0.1 ~ 0.3 |
| 2'-(2-acetamido-2-deoxy-β-D-glucopyranosyloxy)-4,4',6'-trimethoxychalcone | 3 ~ 10 |
| 2'-(benzyloxycarbonyloxy)-4,4',6'-trimethoxychalcone | 0.01 ~ 0.03 |
| 2',4,4'-trimethoxy-6'-(triethylammonioacetoxy)chalcone chloride | 0.01 |
| 2',4,4'-trimethoxy-6'-(4-methoxybenzoyloxy)chalcone | 0.03 ~ 0.1 |
| 2'-(2,4-dimethoxybenzoyloxy)-4,4',6'-trimethoxychalcone | 0.03 ~ 0.1 |
| 2'-(benzoyloxy)-4,4',6'-trimethoxychalcone | 0.03 ~ 0.1 |
| 2'-(furoyloxy)-4,4',6'-trimethoxychalcone | 0.03 |
| 2'-hydroxy-4',6'-dimethoxy-4-(methoxymethoxy)chalcone | 0.03 ~ 0.1 |
| 3-(5-benzimidazolyl)-2'-hydroxy-4',6'-dimethoxyacrylophenone | 0.1 ~ 0.3 |
| 4-acetoxy-2'-hydroxy-4',6'-dimethoxychalcone | 0.3 |

EXAMPLE 23

The antiviral activities of compounds of the invention were tested against lethal infection of Coxsackie virus B1 in mice. ddy Mice weighing about 15 g were infected intraperitoneally (i.p.) by about $LD_{50}$ of the virus. The infected mice were then administered 4 times with the compounds either by oral (p.o.) or intravenous (i.v.) route at -2, 7, 22 and 31 hrs. after infection. The survivals were recorded up to 21 days.

EXAMPLE 24

The test results of Example 23 are shown in Table 2. As shown in Table 2, the compounds tested inhibit the viral infection. Non-treated mice died at 3 to 5 days after infection.

TABLE 2

Antiviral activity against Coxsackievirus B1 in mice

| Compounds | Dose route | % Survival |
|---|---|---|
| 2',4,4'-trimethoxy-6'-(phosphonooxy)chalcone | 80 mg/kg × 4 p.o. | 70 |
|  | 40 | 50 |
|  | 20 | 10 |
| none |  | 0 |
| 2',4,4'-trimethoxy-6'-(phosphonooxy)chalcone | 10 mg/kg × 4 i.v. | 60 |
|  | 5 | 20 |
| none |  | 0 |
| 2'-ethoxy-4,4'-dimethoxy-6'-(phosphonooxy)chalcone | 40 mg/kg × 4 p.o. | 30 |
| none |  | 0 |

EXAMPLE 25

Table 3 shows data on the compounds of the invention concerning acute toxicity in mice.

TABLE 3

| | $LD_{50}$ (mg/kg)[1] | |
|---|---|---|
| Compounds | i.p. route[2] | p.o. route[3] |
| 2',4,4'-trimethoxy-6'-(phosphonooxy)chalcone | >500 | >1,000 |
| 4-ethoxy-2',4'-dimethoxy-6'-(phosphonooxy)chalcone | >500 | >1,000 |
| 2',4'-dimethoxy-4-methyl-6'-(phosphonooxy)chalcone | >500 | >2,000 |
| 2',4'-dimethoxy-4-(methylthio)-6'-(phosphonooxy)chalcone | >500 | >1,000 |
| 2'-ethoxy-4,4'-dimethoxy-6'-(phosphonooxy)chalcone | >500 | >1,000 |
| 2',4'-dimethoxy-3-(5-methyl-2-furyl)-6'-(phosphonooxy)acrylophenone | >500 | >1,200 |
| 4'-ethoxy-2',4-dimethoxy-6'-(phosphonooxy)chalcone | >500 | >2,000 |
| 2',4'-dimethoxy-3,4-(methylenedioxy)-6'-(phosphonooxy)chalcone | >500 | >1,000 |
| 2',4'-dimethoxy-6'-(phosphonooxy)-3-(2-thienyl)acrylophenone | >500 | >1,000 |
| 2'-(2-acetamido-2-deoxy-3,3,6-tri-O-acetyl-β-D-glucopyranoxyloxy)-4,4',6'-trimethoxychalcone | >500 | >2,000 |
| 2'-(2-acetamido-2-deoxy-β-D-glucopyrano- | | |

TABLE 3-continued

| Compounds | LD$_{50}$ (mg/kg)[1] i.p. route[2] | p.o. route[3] |
|---|---|---|
| syloxy)-4,4',6'-trimethoxychalcone | >300 | >2,000 |
| 2'-(benzyloxycarbonyloxy)-4,4',6'-trimethoxychalcone | >500 | >1,000 |
| 2',4,4'-trimethoxy-6'-(triethylammonioacetoxy)chalcone chloride | 180 | >1,000 |
| 2',4,4'-trimethoxy-6'-(4-methoxybenzoyloxy)chalcone | >500 | >1,000 |
| 2'-(2,4-dimethoxybenzoyloxy)-4,4',6'-trimethoxychalcone | >500 | >1,000 |
| 2'-(benzoyloxy)-4,4',6'-trimethoxychalcone | >500 | >1,000 |
| 2'-(furoyloxy)-4,4',6'-trimethoxychalcone | >500 | >1,000 |
| 2'-hydroxy-4',6'-dimethoxy-4-(methoxymethoxy)chalcone | >500 | >1,000 |
| 3-(5-benzimidazolyl)-2'-hydroxy-4',6'-dimethoxyacrylophenone | >100 | >1,000 |
| 4-acetoxy-2'-hydroxy-4',6'-dimethoxychalcone | >500 | >1,000 |

[1]ddy mice weighing 15 ∼ 20 g were administered intraperitoneally with a single dose of the compound. Survivers were recorded on day 21.
[2]Compounds were dissolved in dimethylsulfoxide.
[3]Compounds were suspended with solution of 0.5% by volume carboxymethyl cellulose.

The following Examples 26–29 illustrate various preparations for the inventive compounds. In the Examples, the active ingredient is any compound within formula I, such as the compounds formed in Examples 1–20.

EXAMPLE 26

| Tablets | mg./tablet |
|---|---|
| Active Ingredient | 300 |
| Dried Lactose | 200 |
| Microcrystalline Cellulose | 30 |
| Polyvinyl Pyrrolidone | 5 |
| Magnesium Stearate | 4 |
|  | 539 |

Procedure:
1. Prepare the solution of Item 4 in alcohol or water.
2. Mix Items 1 and 2 in a suitable mixer and granulate with Item 4. Dry overnight.
3. Add Item 3 to the granulation and mix for 10 minutes. Add Item 5 and mix for 3 minutes. Compress on suitable tablet machine.

EXAMPLE 27

Drops for intranasal application containing per 1 ml.

| Active Ingredient (mg) | 0.001 | 0.01 | 0.1 | 1.0 |
|---|---|---|---|---|
| Benzalkonium Chloride (mg) | 0.1 | 0.125 | 0.15 | 0.2 |
| Propylene Glycol/water (1:1 v/v q.s.) (ml) | 1 | 1 | 1 | 1 |

Procedure:
Dissolve Items 1 and 2 in Item 3. Mix well.

EXAMPLE 28

| Troches | |
|---|---|
| Active Ingredient | 0.1 g |
| Powder Sucrose | 1.6 g |
| Acacia | 0.2 g |
| Dextrin | 0.1 g |
| Flavor | 0.001 g |

Procedure:
1. Mix Items 1, 2, 3, 4 and 5 and wet with water until pliable mass is formed.
2. The mass is rolled out and the troche pieces are cut and allowed to dry.

EXAMPLE 29

| Troches | |
|---|---|
| Active Ingredient | 0.1 g |
| DiPac | 1.6 g |
| Acacia | 0.2 g |
| Flavor | 0.001 g |
| Magnesium Stearate | 0.025 g |

Procedure:
1. Mix Items 1, 2, 3 and 4 for 30 minutes.
2. Add Item 5 and mix for 5 minutes.
3. Compress on suitable press.

We claim:
1. A compound of the formula:

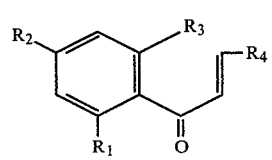

wherein $R_1$ is phosphonooxy, aminoglycosyloxy or acylaminoglycosyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, methylthio, methylenedioxy, acetoxy or methoxymethoxy, or pharmaceutically acceptable salts thereof.

2. The compound of claim 1 wherein $R_4$ is benzimidazolyl.

3. The compound of claim 2 wherein $R_4$ is 5-benzimidazolyl.

4. The compound of claim 1 wherein $R_4$ is furyl which is unsubstituted or substituted with lower alkyl.

5. The compound of claim 4 wherein $R_4$ is 2-furyl which is unsubstituted or substituted with lower alkyl.

6. The compound of claim 5 wherein the compound is 2',4'-dimethoxy-3-(5-methyl-2-furyl)-6'-(phosphonooxy)acrylophenone.

7. The compound of claim 1 wherein $R_4$ is thienyl which is unsubstituted or substituted with lower alkyl.

8. The compound of claim 7 wherein $R_4$ is 2-thienyl which is unsubstituted or substituted with lower alkyl.

9. The compound of claim 8 wherein the compound is 2',4'-dimethoxy-6'-(phosphonooxy)-3-(2-thienyl)acrylophenone.

10. The compound of claim 1 wherein $R_4$ is phenyl which is substituted with lower alkyl, lower alkoxy, alkylthio, alkylenedioxy, acyloxy or alkoxyalkoxy.

11. The compound of claim 1 wherein $R_4$ is dimethoxyphenyl.

12. The compound of claim 10 wherein the compound is 2',4,4'-trimethoxy-6'-(phosphonooxy)chalcone.

13. The compound of claim 10 wherein the compound is 4-ethoxy-2',4'-dimethoxy-6'-(phosphonooxy)chalcone.

14. The compound of claim 10 wherein the compound is 2′,4′-dimethoxy-4-methyl-6′-(phosphonooxy)-chalcone.

15. The compound of claim 10 wherein the compound is 2′,4′-dimethoxy-4-(methylthio)-6′-(phosphonooxy)chalcone.

16. The compound of claim 10 wherein the compound is 2′-ethoxy-4,4′-dimethoxy-6′-(phosphonooxy)-chalcone.

17. The compound of claim 10 wherein the compound is 4′-ethoxy-2′,4-dimethoxy-6′-(phosphonooxy)-chalcone.

18. The compound of claim 10 wherein the compound is 2′,4′-dimethoxy-3,4-(methylenedioxy)-6′-(phosphonooxy)chalcone.

19. The compound of claim 10 wherein the compound is 2′-(2-acetamido-2-deoxy-3,4,6-tri-O-acetyl-β-D-glycopyranosyloxy)-4,4′,6′-trimethoxychalcone.

20. The compound of claim 10 wherein the compound is 2′-(2-acetamido-2-deoxy-β-D-glucopyranosyloxy)-4,4′,6′-trimethoxychalcone.

21. The compound of claim 1 wherein $R_1$ is phosphonooxy.

22. A compound of the formula:

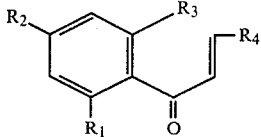

wherein $R_1$ is phosphonooxy; $R_2$ and $R_3$ each are lower alkoxy; and $R_4$ is 5-benzimidazolyl, 2-furyl, 5-methyl-2-furyl, 2-thienyl or p-tolyl, p-methoxyphenyl or o-p-dimethoxyphenyl, or pharmaceutically acceptable salts thereof.

23. A compound of the formula:

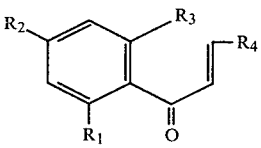

wherein $R_1$ is phosphonooxy, $R_2$ and $R_3$ each are lower alkoxy and $R_4$ is phenyl which is substituted with lower alkoxy.

24. An anti-enteroviral composition comprising:
(a) as an active ingredient a compound of the formula:

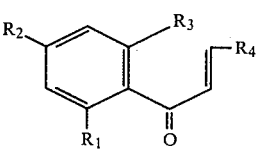

wherein $R_1$ is phosphonooxy, aminoglycosyloxy or acylaminoglycosyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, methylthio, methylenedioxy, acetoxy or methoxymethoxy, or pharmaceutically acceptable salts thereof in an amount which is effective as an anti-enteroviral agent, and
(b) a pharmaceutically acceptable carrier material.

25. An anti-rhinoviral composition comprising:
(a) as an active ingredient a compound of the formula:

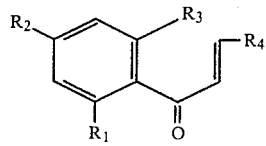

wherein $R_1$ is phosphonooxy, aminoglycosyloxy or acylaminoglycosyloxy; $R_2$ and $R_3$ each are lower alkoxy; and $R_4$ is benzimidazolyl, furyl which is unsubstituted or substituted with lower alkyl, thienyl which is unsubstituted or substituted with alkyl, or phenyl which is substituted with lower alkyl, lower alkoxy, methylthio, methylenedioxy, acetoxy or methoxymethoxy, or pharmaceutically acceptable salts thereof in an amount which is effective as an anti-rhinoviral agent, and
(b) a pharmaceutically acceptable carrier material.

26. The composition of claim 24 or 25 wherein $R_4$ is benzimidazole.

27. The composition of claim 26 wherein $R_4$ is 5-benzimidazole.

28. The composition of claim 24 or 25 wherein $R_4$ is furyl which unsubstituted or substituted with lower alkyl.

29. The composition of claim 28 wherein $R_4$ is 2-furyl which is unsubstituted or substituted with lower alkyl.

30. The composition of claim 29 wherein the compound is 2′,4′-dimethoxy-3-(5-methyl-2-furyl)-6′-(phosphonooxy)acrylophenone.

31. The composition of claim 24 or 25 wherein $R_4$ is thienyl which is unsubstituted or substituted with lower alkyl.

32. The composition of claim 31 wherein $R_4$ is 2-thienyl which is unsubstituted or substituted with lower alkyl.

33. The composition of claim 32 wherein the compound is 2′,4′-dimethoxy-6′-(phosphonooxy)-3-(2-thienyl)acrylophenone.

34. The composition of claim 24 or 25 wherein $R_4$ is phenyl which is substituted with lower alkyl, lower alkoxy, alkylthio, alkylenedioxy, acyloxy or alkoxyalkoxy.

35. The composition of claim 34 wherein $R_4$ is dimethoxyphenyl.

36. The composition of claim 34 wherein the compound is 2′,4,4′-trimethoxy-6′-(phosphonooxy)chalcone.

37. The composition of claim 34 wherein the compound is 4-ethoxy-2′,4′-dimethoxy-6′-(phosphonooxy)-chalcone.

38. The composition of claim 34 wherein the compound is 2,4′-dimethoxy-4-methyl-6′-(phosphonooxy)-chalcone.

39. The composition of claim 34 wherein the compound is 2′,4′-dimethoxy-4-(methylthio)-6′-(phosphonooxy)chalcone.

40. The composition of claim 34 wherein the compound is 2′-ethoxy-4,4′-dimethoxy-6′-(phosphonooxy)-chalcone.

41. The composition of claim 34 wherein the compound is 4'-ethoxy-2',4-dimethoxy-6'-(phosphonooxy)-chalcone.

42. The composition of claim 34 wherein the compound is 2',4'-dimethoxy-3,4-(methylenedioxy)-6'-(phosphonooxy)chalcone.

43. The composition of claim 34 wherein the compound is 2'-(2-acetamido-2-deoxy-3,4,6-tri-O-acetyl-β-D-glucopyranosyloxy)-4,4'6'-trimethoxychalcone.

44. The composition of claim 34 wherein the compound is 2'-(2-acetamido-2-deoxy-β-D-glucopyranosyloxy)-4,4'6'-trimethoxychalcone.

45. The composition of claim 24 or 25 wherein $R_1$ is phosphonooxy.

46. The composition of claim 24 wherein compound I amounts to about 0.001% to about 70.0% by weight of the anti-enteroviral composition.

47. The composition of claim 25 wherein compound I amounts to about 0.001% to about 70.0% by weight of the anti-rhinoviral composition.

48. A method for treating a mammal infected by an enterovirus comprising administering to said mammal a compound of the formula:

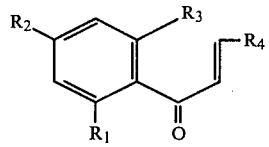

wherein $R_1$ is phosphonooxy, aminoglycosyloxy or acylaminoglycosyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl, or phenyl which is substituted with lower alkyl, lower alkoxy, methylthio, methylenedioxy, acetoxy or methoxymethoxy, or pharmaceutically acceptable salts thereof in an amount which is effective as an anti-enteroviral agent.

49. A method for treating a mammal infected by a rhinovirus comprising administering to said mammal a compound of the formula:

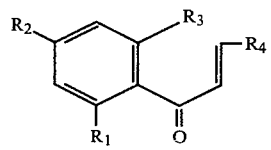

wherein $R_1$ is phosphonooxy, aminoglycosyloxy or acylaminoglycosyloxy; $R_2$ and $R_3$ each are lower alkoxy; and $R_4$ is benzimidazolyl, furyl which is unsubstituted or substituted with lower alkyl, thienyl which is unsubstituted or substituted with lower alkyl or phenyl which is substituted with lower alkyl, lower alkoxy, methylthio, methylenedioxy, acetoxy or methoxymethoxy, or pharmaceutically acceptable salts thereof in an amount which is effective as an anti-rhinoviral agent.

50. The method of claim 48 or 49 wherein the compound is 4'-ethoxy-2',4-dimethoxy-6'-(phosphonooxy)-chalcone.

51. The method of claim 48 or 49 wherein compound I is administered at a daily dose of about 1 mg. to about 100 mg. per kilogram of body weight of said mammal.

52. The method of claim 50 wherein compound I is administered by intranasal application.

* * * * *